United States Patent
Koh

(10) Patent No.: US 7,785,256 B1
(45) Date of Patent: Aug. 31, 2010

(54) METHOD AND SYSTEM FOR DISPLAYING PATIENT ACTIVITY DATA USING POINCARÉ AND INTENSITY PLOT

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 824 days.

(21) Appl. No.: 11/329,671

(22) Filed: Jan. 11, 2006

(51) Int. Cl.
*A61B 5/00* (2006.01)
(52) U.S. Cl. .................. 600/300; 128/920
(58) Field of Classification Search .......... 600/300, 600/301; 128/903–905, 920
See application file for complete search history.

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PT |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 4,969,467 A | 11/1990 | Callaghan et al. | 128/419 PG |
| 5,350,410 A | 9/1994 | Kleks et al. | 607/28 |
| 5,622,178 A * | 4/1997 | Gilham | 600/523 |
| 6,045,513 A | 4/2000 | Stone et al. | 600/508 |
| 6,102,874 A | 8/2000 | Stone et al. | 600/595 |
| 6,275,734 B1 | 8/2001 | McClure et al. | 607/27 |
| 6,280,409 B1 | 8/2001 | Stone et al. | 604/67 |
| 6,616,608 B2 * | 9/2003 | Honda et al. | 600/301 |
| 7,038,595 B2 * | 5/2006 | Seely | 340/870.07 |
| 2002/0161412 A1 | 10/2002 | Sun et al. | 607/19 |
| 2005/0076909 A1 * | 4/2005 | Stahmann et al. | 128/204.23 |

FOREIGN PATENT DOCUMENTS

WO     WO 99/58056     11/1999

OTHER PUBLICATIONS

Kadhiresan, Veerichetty A. MD et al., "A Novel Method—The Activity Log Index—for Monitoring Physical Activity of Patients with Heart Failure," *The American Journal of Cardiology*, vol. 89 (Jun. 15, 2002), pp. 1435-1437.

* cited by examiner

*Primary Examiner*—Michael C Astorino
*Assistant Examiner*—Kai Rajan

(57) ABSTRACT

Methods and systems are presented for displaying patient activity data from implantable cardiac device (ICD). The method includes: sensing an activity level, storing the sensed activity level as a first coordinate of an activity data point, generating an average activity level from a predetermined number of sensed activity levels, storing the average activity level as a second coordinate of the activity data point, accumulating a number of times the activity data point having the first and second coordinates occurs, and storing the accumulated number of times. These steps are repeated for a predetermined period of time, and a plurality of activity data points each having an associated accumulated number of times is stored. The method further includes graphically displaying each of the plurality of activity data points with the associated accumulated number of times.

11 Claims, 8 Drawing Sheets

INTERPRETATION BASED ON LOCATION

INTERPRETATION BASED ON COLOR MAP

INTERPRETATION BASED ON DIAMETER

INTERPRETATION BASED ON HEIGHT

METHOD AND SYSTEM FOR DISPLAYING PATIENT ACTIVITY DATA USING POINCARÉ AND INTENSITY PLOT

FIELD OF THE INVENTION

The present invention relates generally to implantable cardiac devices and, more particularly, to methods and systems for displaying patient activity data from an implantable cardiac device.

BACKGROUND

Conventional implantable medical devices typically include activity sensors, such as accelerometers, piezoelectric sensors, and the like, that generate activity signals related to the movement of a patient. Such activity signal data can be accumulated over a period of time to allow a clinician to assess a patient's level of activity. For example, a clinician might monitor a patient's level of activity in response to delivery of a particular therapy. As activity signal data points accumulate (e.g., six months is a typical clinical follow-up duration), clinicians will often ignore any data trends because of poor graphical user interfaces (GUI) that are not designed to depict the large amount of activity signal data, which will accumulate over a typical clinical follow-up duration.

What is needed, therefore, are improved systems and methods for displaying patient activity data from an implantable cardiac device in a format that enables clinicians to more easily identify data trends in accumulated activity signal data.

BRIEF SUMMARY

Methods and systems are presented for displaying patient activity data from an implantable cardiac device (ICD).

In a first exemplary embodiment, a method for displaying patient activity data includes: (a) sensing an activity level, and storing the sensed activity level as a first coordinate of an activity data point; (b) generating an average activity level from a predetermined number of sensed activity levels, and storing the average activity level as a second coordinate of the activity data point; and (c) accumulating a number of times the activity data point having the first and second coordinates occurs, and storing the accumulated number of times. The method further includes repeating steps (a)-(c) for a predetermined period of time, and storing a plurality of activity data points each having an associated accumulated number of times. The method further includes graphically displaying each of the plurality of activity data points with the associated accumulated number of times.

In a second exemplary embodiment, a system for displaying patient activity data includes an ICD and a graphical user interface. The ICD includes: a memory, at least one sensor that senses an activity level, and a processor that generates an average activity level from a predetermined number of sensed activity levels. The sensed activity level is stored in the memory as a first coordinate of an activity data point, and the average activity level is stored in the memory as a second coordinate of the activity data point. The processor further accumulates a number of times the activity data point having the first and second coordinates occurs. The accumulated number of times is stored in the memory. The graphical user interface retrieves from the memory of the ICD a plurality of activity data points, each having an associated accumulated number of times, and graphically displays each of the plurality of activity data points with the associated accumulated number of times.

In a third exemplary embodiment, a system for displaying patient activity data includes storage means for storing the patient activity data, sensor means for sensing an activity level, and processing means for generating an average activity level from a predetermined number of sensed activity levels. The storage means stores the sensed activity level as a first coordinate of an activity data point and stores the average activity level as a second coordinate of the activity data point. The processing means further accumulates a number of times the activity data point having the first and second coordinates occurs, and the storage means further stores the accumulated number of times. The system further includes display means for retrieving from the storage means a plurality of activity data points, each having an associated accumulated number of times, and graphically displaying each of the plurality of activity data points with the associated accumulated number of times.

Further features and advantages of the methods and systems presented herein, as well as the structure and operation of various example methods and systems, are described in detail below with reference to the accompanying drawings.

BRIEF DESCRIPTION OF THE DRAWINGS/FIGURES

The accompanying drawings, which are incorporated herein and form part of the specification, illustrate the methods and systems presented herein for displaying patient activity data from an implantable cardiac device. Together with the description, the drawings further serve to explain the principles of and to enable a person skilled in the relevant art(s) to make and use the methods and systems presented herein. In the drawings, like reference numbers indicate identical or functionally similar elements, and the drawing in which an element first appears is typically indicated by the leftmost digit(s) in the corresponding reference number.

DETAILED DESCRIPTION

Overview

The following detailed description of methods and systems for displaying patient activity data from an implantable cardiac device (ICD) refers to the accompanying drawings that illustrate exemplary embodiments consistent with these methods and systems. Other embodiments are possible, and modifications may be made to the embodiments within the spirit and scope of the methods and systems presented herein. Therefore, the following detailed description is not meant to limit the methods and systems described herein. Rather, the scope of these methods and systems is defined by the appended claims.

It would be apparent to one of skill in the art that the methods and systems for displaying patient activity data from an ICD, as described below, may be implemented in many different embodiments of hardware, software, firmware, and/or the entities illustrated in the figures. Any actual software and/or hardware described herein is not limiting of these methods and systems. Thus, the operation and behavior of the methods and systems will be described with the understanding that modifications and variations of the embodiments are possible, given the level of detail presented herein.

Figure 1:
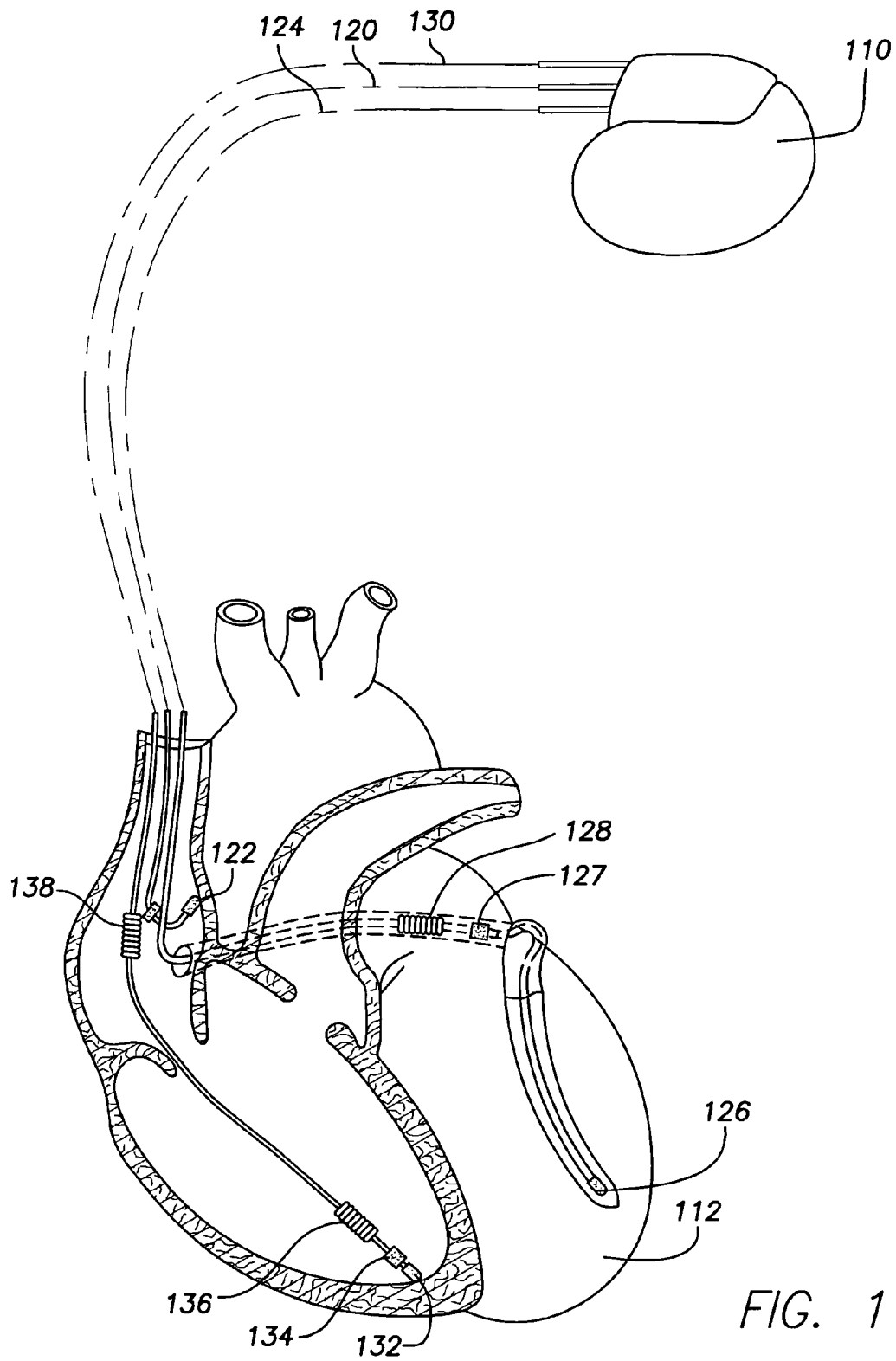
FIG. 1 is a simplified diagram illustrating an example ICD in electrical communication with a patient's heart by means of three leads suitable for delivering multi-chamber stimulation and pacing therapy.
Figure 2:
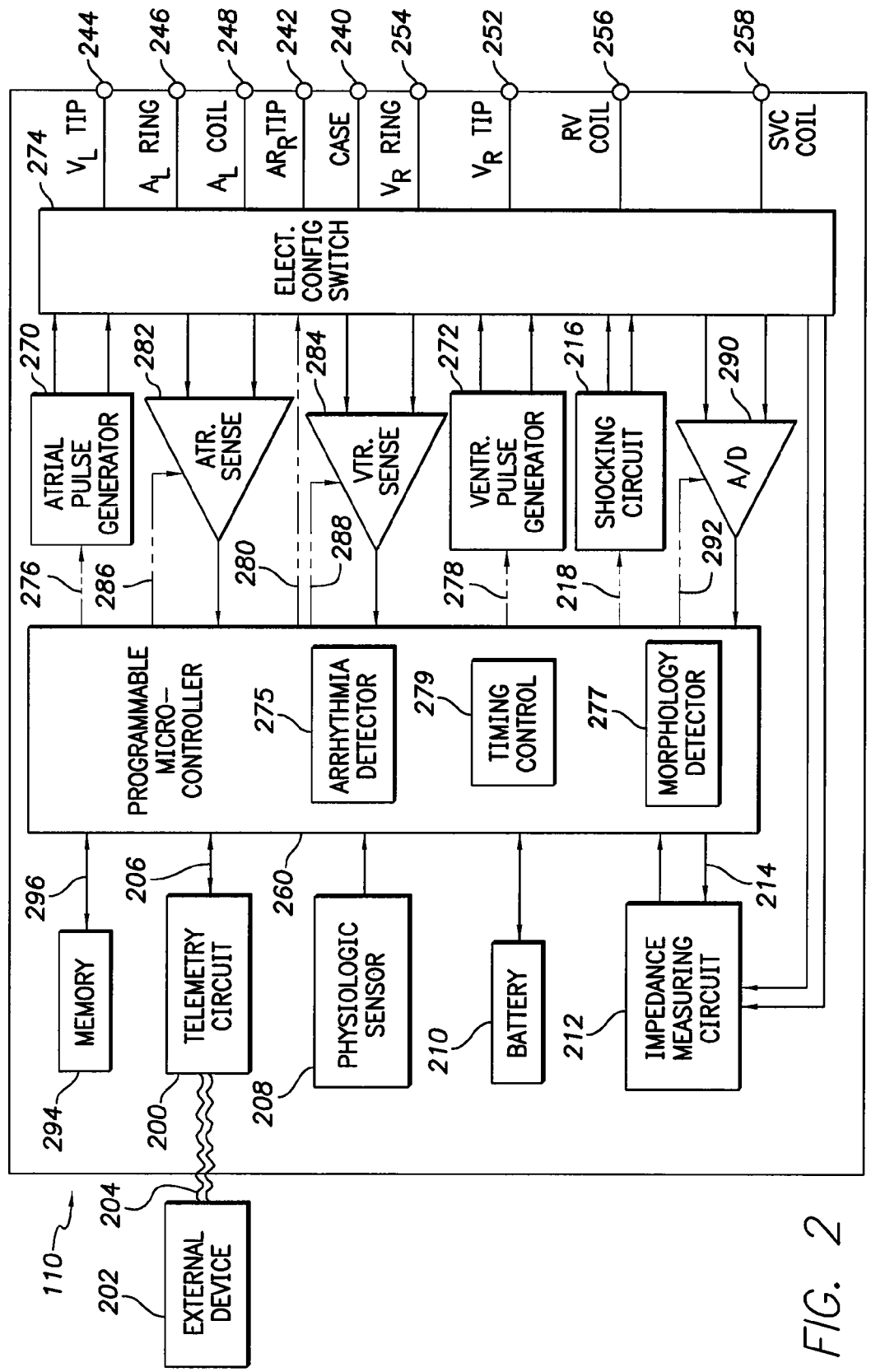
FIG. 2 is a functional block diagram of an example ICD that can provide cardioversion, defibrillation, and pacing stimulation in four chambers of a heart.

Before describing the methods and systems for displaying patient activity data from an ICD in detail, it is helpful to describe an example environment in which these methods and systems may be implemented. The methods and systems described herein are particularly useful in the environment of an ICD. An ICD is a medical device that is implanted in a patient to monitor cardiac function and to deliver appropriate electrical therapy, for example, pacing pulses, cardioverting and defibrillator pulses, and drug therapy, as required. ICDs include, for example, pacemakers, cardioverters, defibrillators, implantable cardioverter defibrillators, implantable cardiac rhythm management devices, and the like. The term "implantable cardiac device" or simply "ICD" is used herein to refer to any implantable cardiac device. FIGS. 1-2 illustrate such an environment including the methods and systems for displaying patient activity data from an ICD described herein.

Exemplary ICD in Electrical Communication with a Patient's Heart

FIG. 1 illustrates an exemplary ICD 110 in electrical communication with a patient's heart 112 by way of three leads, 120, 124 and 130, suitable for delivering multi-chamber stimulation and pacing therapy. To sense atrial cardiac signals and to provide right atrial chamber stimulation therapy, ICD 110 is coupled to implantable right atrial lead 120 having at least an atrial tip electrode 122, which typically is implanted in the patient's right atrial appendage.

To sense left atrial and ventricular cardiac signals and to provide left-chamber pacing therapy, ICD 110 is coupled to "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 124 is designed to receive atrial and ventricular cardiac signals and to deliver left ventricular pacing therapy using at least a left ventricular tip electrode 126, left atrial pacing therapy using at least a left atrial ring electrode 127, and shocking therapy using at least a left atrial coil electrode 128. ICD 110 is also shown in electrical communication with the patient's heart 112 by way of implantable right ventricular lead 130 having, in this embodiment, a right ventricular tip electrode 132, a right ventricular ring electrode 134, a right ventricular (RV) coil electrode 136, and a superior vena cava (SVC) coil electrode 138. Typically, right ventricular lead 130 is transvenously inserted into heart 112 so as to place right ventricular tip electrode 132 in the right ventricular apex so that RV coil electrode 136 will be positioned in the right ventricle and SVC coil electrode 138 will be positioned in the SVC. Accordingly, right ventricular lead 130 is capable of receiving cardiac signals and delivering stimulation in the form of pacing and shock therapy to the right ventricle.

Functional Elements of an Exemplary ICD

FIG. 2 shows a simplified block diagram of ICD 110, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 240 of ICD 110, shown schematically in FIG. 2, is often referred to as the "can," "case" or "case electrode" and may be programmably selected to act as the return electrode for all "unipolar" modes. Housing 240 may further be used as a return electrode for shocking purposes alone or in combination with one or more of coil electrodes, 128, 136, and 138, which are shown in FIG. 1. Housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal (AR TIP) 242 adapted for connection to atrial tip electrode 122 (shown in FIG. 1).

To achieve left chamber sensing, pacing and shocking, the connector includes at least a left ventricular tip terminal (VL TIP) 244, a left atrial ring terminal (AL RING) 246, and a left atrial shocking terminal (AL COIL) 248, which are adapted for connection to left ventricular ring electrode 126, left atrial tip electrode 127, and left atrial coil electrode 128 (all shown in FIG. 1), respectively.

To support right chamber sensing, pacing, and shocking the connector also includes a right ventricular tip terminal (VR TIP) 252, a right ventricular ring terminal (VR RING) 254, a right ventricular shocking terminal (RV COIL) 256, and an SVC shocking terminal (SVC COIL) 258, which are configured for connection to right ventricular tip electrode 132, right ventricular ring electrode 134, RV coil electrode 136, and SVC coil electrode 138 (all shown in FIG. 1), respectively.

At the core of ICD 110 is a programmable microcontroller 260, which controls the various modes of stimulation therapy. As is well known in the art, microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 260 includes the ability to process or monitor input signals (data) as controlled by a program code stored in a designated block of memory. The details of the design of microcontroller 260 are not critical to the techniques presented herein. Rather, any suitable microcontroller 260 can be used to carry out the functions described herein. The use of microprocessor-based control circuits for performing timing and data analysis functions are well known in the art.

Representative types of control circuitry that may be used with the techniques presented herein include the microprocessor-based control system of U.S. Pat. No. 4,940,052 (Mann et. al.) and the state-machines of U.S. Pat. Nos. 4,712,555 (Thornander et al.) and 4,944,298 (Sholder). For a more detailed description of the various timing intervals used within ICDs and their inter-relationship, see U.S. Pat. No. 4,788,980 (Mann et. al.). The '052, '555, '298 and '980 patents are incorporated herein by reference.

As shown in FIG. 2, an atrial pulse generator 270 and a ventricular pulse generator 272 generate pacing stimulation pulses for delivery by right atrial lead 120, right ventricular lead 130, and/or coronary sinus lead 124 (shown in FIG. 1) via an electrode configuration switch 274. It is understood that in order to provide stimulation therapy in each of the four chambers of the heart, atrial and ventricular pulse generators 270 and 272 may include dedicated, independent pulse generators, multiplexed pulse generators, or shared pulse generators. Pulse generators 270 and 272 are controlled by microcontroller 260 via appropriate control signals 276 and 278, respectively, to trigger or inhibit the stimulation pulses.

Microcontroller 260 further includes timing control circuitry 279, which is used to control pacing parameters (e.g., the timing of stimulation pulses) as well as to keep track of the timing of refractory periods, post ventricular atrial refractory period (PVARP) intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 274 includes a plurality of switches for connecting the desired electrodes to the appropriate I/O circuits, thereby providing complete electrode programmability. Accordingly, switch 274, in response to a control signal 280 from microcontroller 260, determines the polarity of the stimulation pulses (e.g., unipolar, bipolar, combipolar, etc.) by selectively closing the appropriate combination of switches (not shown) as is known in the art.

Atrial sensing (ATR. SENSE) circuits 282 and ventricular sensing (VTR. SENSE) circuits 284 may also be selectively coupled to right atrial lead 120, coronary sinus lead 124, and right ventricular lead 130, which are shown in FIG. 1, through switch 274 for detecting the presence of cardiac activity in each of the four chambers of the heart. Accordingly, atrial and ventricular sensing circuits 282 and 284 may include dedicated sense amplifiers, multiplexed amplifiers, or shared amplifiers. Switch 274 determines the "sensing polarity" of the cardiac signal by selectively closing the appropriate switches, as is also known in the art. In this way, a clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 110 to deal effectively with the difficult problem of sensing the low amplitude signal characteristics of atrial or ventricular fibrillation. Such sensing circuits, 282 and 284, can be used to determine cardiac performance values used in the techniques presented herein.

The outputs of atrial and ventricular sensing circuits 282 and 284 are connected to microcontroller 260 which, in turn, are able to trigger or inhibit atrial and ventricular pulse generators, 270 and 272, respectively, in a demand fashion in response to the absence or presence of cardiac activity, in the appropriate chambers of the heart. Sensing circuits 282 and 284, in turn, receive control signals over signal lines 286 and 288 from microcontroller 260 for purposes of measuring cardiac performance at appropriate times, and for controlling the gain, threshold, polarization charge removal circuitry (not shown), and timing of any blocking circuitry (not shown) coupled to the inputs of sensing circuits 282 and 286.

For arrhythmia detection, ICD 110 utilizes the atrial and ventricular sensing circuits 282 and 284 to sense cardiac signals to determine whether a rhythm is physiologic or pathologic. The timing intervals between sensed events (e.g., P-waves, R-waves, and depolarization signals associated with fibrillation, which are sometimes referred to as "F-waves" or "Fib-waves") are then classified by microcontroller 260 by comparing them to a predefined rate zone limit (i.e., bradycardia, normal, low rate ventricular tachycardia (VT), high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Microcontroller 260 utilizes arrhythmia detection circuitry 275 and morphology detection circuitry 277 to recognize and classify arrhythmia so that appropriate therapy can be delivered.

Cardiac signals are also applied to the inputs of an analog-to-digital (ND) data acquisition system 290. Data acquisition system 290 is configured to acquire electrical activity signals, such as EGM signals, convert the raw analog data into a digital signal, and store the digital signals for later processing and/or telemetric transmission to an external device 202. In FIG. 2, data acquisition system 290 is coupled to right atrial lead 120, coronary sinus lead 124, and right ventricular lead 130, which are shown in FIG. 1, through switch 274 to sample cardiac signals across any pair of desired electrodes.

Advantageously, data acquisition system 290 can be coupled to microcontroller 260, or other detection circuitry, for detecting an evoked response from heart 112 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 260 detects a depolarization signal during a window following a stimulation pulse, the presence of which indicates that capture has occurred. Microcontroller 260 enables capture detection by triggering ventricular pulse generator 272 to generate a stimulation pulse, starting a capture detection window using timing control circuitry 279 within microcontroller 260, and enabling data acquisition system 290 via a control signal 292 to sample the cardiac signal that falls in the capture detection window and, based on the amplitude, determines if capture has occurred.

The implementation of capture detection circuitry and algorithms are well known. See for example, U.S. Pat. No.

4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Kleks et. al.), which patents are hereby incorporated herein by reference. The type of capture detection system used is not critical to the techniques presented herein.

Microcontroller 260 is further coupled to a memory 294 by a suitable data/address bus 296. The programmable operating parameters used by microcontroller 260 are stored and modified, as required, in memory 294 in order to customize the operation of ICD 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 112 within each respective tier of therapy.

Advantageously, the operating parameters of ICD 110 may be non-invasively programmed into memory 294 through a telemetry circuit 200 in telemetric communication with external device 202, such as a programmer, transtelephonic transceiver, or a diagnostic system analyzer. Telemetry circuit 200 is activated by microcontroller 260 by a control signal 206. Telemetry circuit 200 advantageously allows EGMs and status information relating to the operation of ICD 110 (as contained in microcontroller 260 or memory 294) to be sent to external device 202 through an established communication link 204. Telemetry circuit 200 also allows data obtained by an external sensor device to be passed to microcontroller 260 for analysis.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 110 further includes a physiologic sensor 208 that can be used to detect changes in cardiac performance or changes in the physiological condition of the heart. Accordingly, microcontroller 260 can respond by adjusting the various pacing parameters (such as rate, AV Delay, RV-LV Delay, V-V Delay, etc.). Microcontroller 260 controls adjustments of pacing parameters by, for example, controlling the stimulation pulses generated by the atrial and ventricular pulse generators 270 and 272. While shown as being included within ICD 110, it is to be understood that physiologic sensor 208 may also be external to ICD 110, yet still be implanted within or carried by the patient. More specifically, sensor 208 can be located inside ICD 110, on the surface of ICD 110, in a header of ICD 110, or on a lead (which can be placed inside or outside the bloodstream).

ICD 110 further includes a magnet detection circuitry (not shown), coupled to microcontroller 260. It is the purpose of the magnet detection circuitry to detect when a magnet is placed over ICD 110. A clinician may use the magnet to perform various test functions of ICD 110 and/or to signal microcontroller 260 that external device 202 is in place to receive or transmit data to microcontroller 260 through telemetry circuit 200.

As further shown in FIG. 2, ICD 110 is shown as having an impedance measuring circuit 212, which is enabled by microcontroller 260 via a control signal 214. The known uses for an impedance measuring circuit 212 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. Impedance measuring circuit 212 is advantageously coupled to switch 274 so that any desired electrode may be used. Impedance measuring circuit 212 is not critical to the techniques presented herein and is shown only for completeness.

In the case where ICD 110 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 260 further controls a shocking circuit 216 by way of a control signal 218. Shocking circuit 216 generates shocking pulses of low (e.g., up to 0.5 Joules), moderate (e.g., 0.5-10 Joules), or high energy (e.g., 11-40 Joules), as controlled by microcontroller 260. Such shocking pulses are applied to the patient's heart 112 through at least two shocking electrodes (e.g., selected from left atrial coil electrode 128, RV coil electrode 136, and SVC coil electrode 138, which are shown in FIG. 1). As noted above, housing 240 may act as an active electrode in combination with RV electrode 136, or as part of a split electrical vector using SVC coil electrode 138 or left atrial coil electrode 128 (i.e., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognized), and pertaining exclusively to the treatment of fibrillation. Accordingly, microcontroller 260 is capable of controlling the synchronous or asynchronous delivery of the shocking pulses.

ICD 110 additionally includes a battery 210, which provides operating power to a load that includes all of the circuits shown in FIG. 2.

Exemplary System for Displaying Patient Activity Data from an ICD

Figure 3:
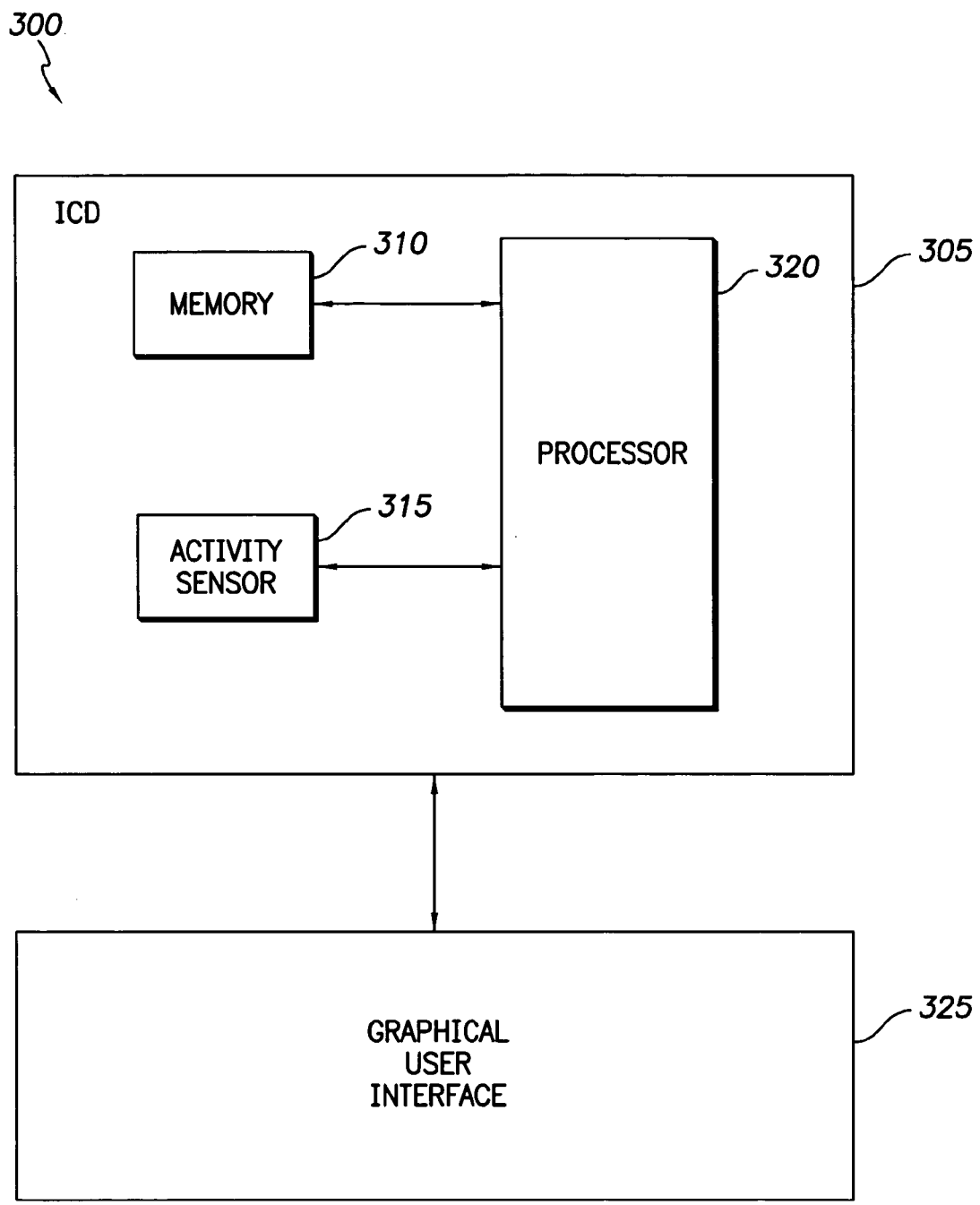
FIG. 3 illustrates an exemplary system for displaying patient activity data from an ICD.

FIG. 3 illustrates an exemplary system 300 for displaying patient activity data from an ICD. System 300 includes an ICD 305 coupled to a graphical user interface 325. For example, system 300 can include exemplary ICD 110 and external device 202, which are illustrated in FIG. 2.

As shown in FIG. 3, ICD 305 includes a processor 320 coupled to a memory 310 and to at least one activity sensor 315. For example, ICD 305 can include memory 294, physiologic sensor 208, and programmable microcontroller 260 of exemplary ICD 110 illustrated in FIG. 2.

Activity sensor 315 senses an activity level related to movement of a patient. For example, activity sensor 315 can include an accelerometer, a piezoelectric sensor, or the like. When a patient moves, the activity sensor senses the movement and generates a signal related to the movement. The sensed activity signals can be accumulated over a period of time to allow a clinician to analyze trends in the patient's activity level (e.g., the clinician might monitor the patient's activity level for a follow-up duration after delivery of a particular therapy). Processor 320 processes sensed activity signals to allow for convenient display to the clinician. In an example implementation, processor 320 processes the sensed activity data to generate a histogram, which can be displayed as an intensity plot superimposed on a Poincaré plot.

Poincaré plots can be used to show relationships between current data and past data. Thus, in an example implementation, processor 320 calculates an average activity level based on a predetermined number of sensed activity levels. In this case, if A(i) corresponds to a sensed activity level at a time i, then processor 320 calculates an average activity level based on N number of previously sensed activity levels (where N>0) as shown below in equation (1).

$$\text{past } N \text{ average} = [A(i) + A(i-1) + A(i-2) + \ldots + A(i-N+1) + A(i-N)]/N \quad (1)$$

The sensed activity level (i.e., A(i)) is stored in memory 310 as a first coordinate (e.g., an x-coordinate) of an activity data point, and the average activity level (i.e., past N average) generated by processor 320 is stored in memory 310 as a second coordinate (e.g., a y-coordinate) of the activity data point. In this way, a Poincaré plot can be displayed with each activity data point (x=A(i), y=past N average) plotted on x and y-axes.

Because a patient's movements are likely to be cyclical (e.g., a patient is likely to repeat many of the same movements on a daily basis), processor 320 also accumulates a number of times each activity data point having particular first and second coordinates occurs. Thus, activity data points having the same coordinates are likely to be generated numerous times. The accumulated number of times for each activity data point having particular first and second coordinates is also stored in memory 310.

For the example described above, each point care Poincaré activity data point (x=A(i), y=past N average) has a corresponding rough grid histogram bin that stores an accumulated count of the same (x=A(i), y=past N average) value. This histogram bin count is updated when a match occurs. Thus, the patient activity data is stored in memory 310 in three-dimensions: the sensed activity level corresponds to a first dimension (e.g., x-axis), the average activity level corresponds to a second dimension (e.g., y-axis), and the accumulated number of times for each activity data point (i.e., the histogram bin count) corresponds to a third dimension (e.g., z-axis). Memory 310 can be implemented with a circular buffer, or cleared to zero at a predetermined interval for simplicity. For example, a sixty-day moving average window can be implemented so that only sixty day's worth of activity data is stored at a time. After each sixty-day period, the buffer can be cleared or, if implemented as a First In First Out (FIFO) buffer, older activity data can be deleted to accommodate newly acquired activity data.

When coupled by telemetry to ICD 305, graphical user interface 325 retrieves from memory 310 a plurality of activity data points each having an associated accumulated number of times. In an example implementation, graphical user interface 325 is a clinician workstation that includes a processor and a display device. Graphical user interface 325 displays each of the plurality of activity data points in conjunction with the associated accumulated number of times (i.e., histogram bin count) in a single presentation.

Figure 7:
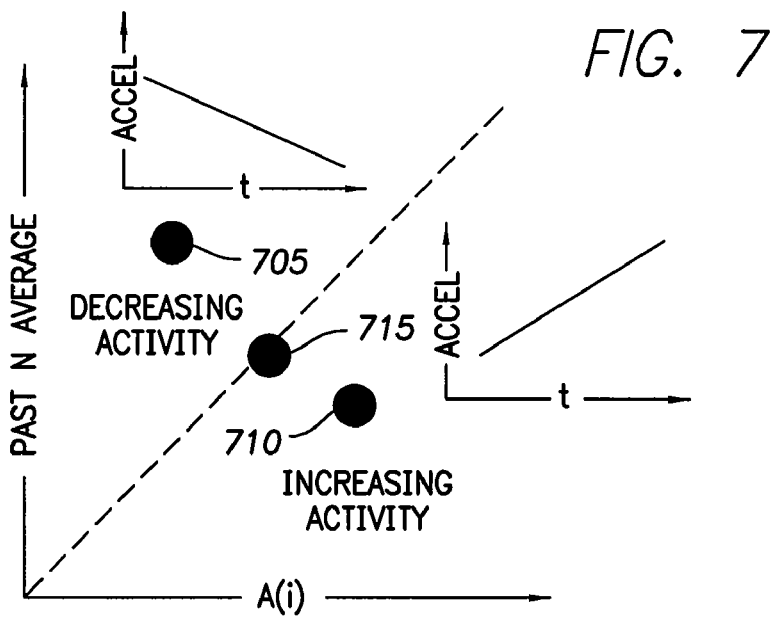
FIG. 7 illustrates an example graphical display and interpretation of accelerometer data showing intensity based on location.
Figure 8:
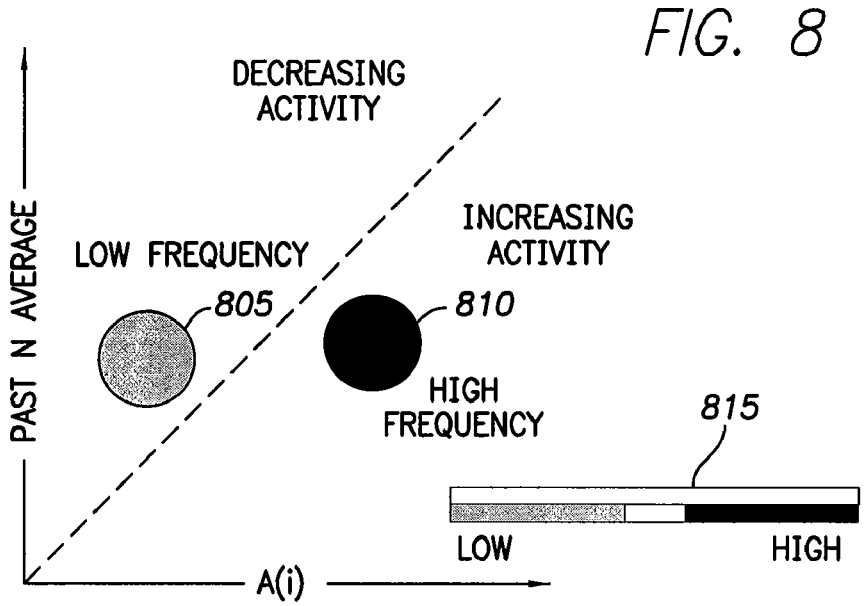
FIG. 8 illustrates an example graphical display and interpretation of accelerometer data showing intensity based on location and endurance based on color map.
Figure 9:
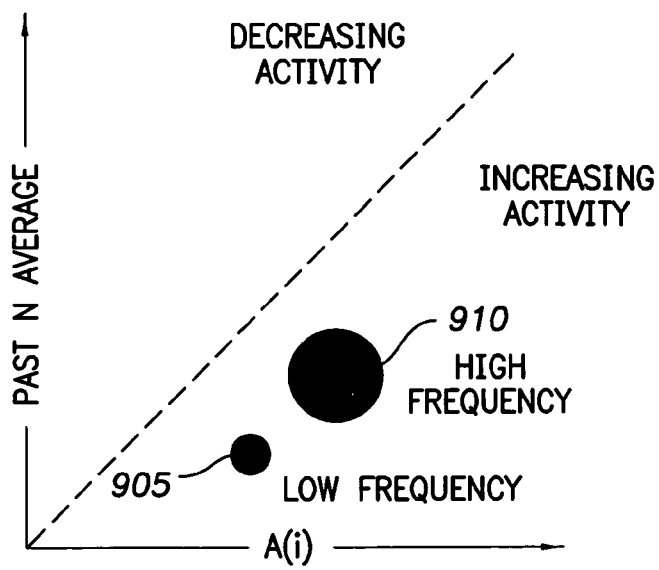
FIG. 9 illustrates an example graphical display and interpretation of accelerometer data showing intensity based on location and endurance based on diameter.
Figure 10:
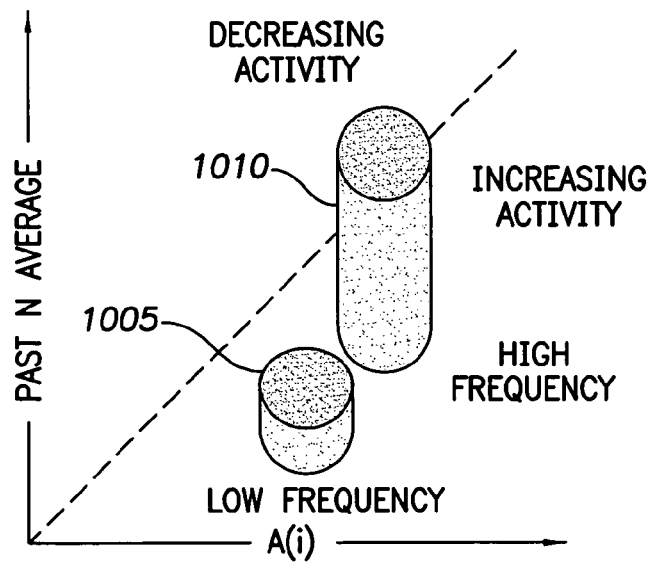
FIG. 10 illustrates an example graphical display and interpretation of accelerometer data showing intensity based on location and endurance based on height.

An advantage of this approach is that intensity (i.e., exercise) and endurance information can be conveniently derived from a single plot. FIGS. 7-10 illustrate plots of example accelerometer activity data. In FIGS. 7-9, the activity data points are plotted in two dimensions, with the sensed activity level (A(i)) on the x-axis (accelerometer unit in mg) and the average activity level for the past N measurements (past N average) on the y-axis. As described below, intensity information can be derived based on the location of the activity data points. In FIGS. 8-9, in addition to the activity data points plotted in two dimensions, accumulated activity data (i.e., histogram bin count) is depicted using color map and diameter, respectively. In FIG. 10, the activity data points are plotted in three dimensions, with the sensed activity level (AN) on the x-axis, the average activity level for the past N measurements (past N average) on the y-axis, and the accumulated activity data (i.e., histogram bin count) on the z-axis. As described below, endurance information can be derived based on the color, diameter, and height, among other features, of the activity data points.

Intensity of activity can be interpreted as shown in FIG. 7. Activity data points located above the y=x line, such as activity data point 705, indicate decreasing activity intensity (i.e., the current activity intensity is lower than the past N activity samples, indicating that the patient's condition is worsening). Activity data points located below the y=x line, such as activity data point 710, indicate increasing intensity (i.e., the current activity intensity is greater than the past N activity samples, indicating that the patient's condition is improving). Activity data points located on the y=x line, such as activity data point 715, indicate unchanged intensity (i.e., the current activity intensity is the same as the past N activity samples, indicating that patient's condition is unchanged).

Endurance of activity can be interpreted as shown in FIGS. 8-10. For large amounts of accumulated patient activity data, the clinician can conveniently display the accumulated activity data point information (i.e., the histogram bin count) in a variety of ways, using two or three dimensions. In one example, shown in FIG. 8, the clinician can display the histogram bin count as a color coded intensity map. In another example, shown in FIGS. 9 and 10, the clinician can display the histogram bin count as a relative size, such as diameter and height, respectively, of a graphical symbol used to indicate each activity data point. As will be understood by one of skill in the art, other graphical symbol features can be varied to depict relative endurance of activity (i.e., exercise) events.

In the example of FIG. 8, the clinician can display the histogram bin count by varying the color of a graphical symbol used to plot each activity data point. In FIG. 8, low endurance (i.e., low frequency) events are represented by circular symbols having different colors than higher endurance (i.e., high frequency) events. In FIG. 8, activity data point 805 represents a lower endurance event than activity data point 810 because, according to a color scale 815, the color of the graphical symbol for activity data point 805 is on the lower end of color scale 815 (e.g., light blue, illustrated in FIG. 8 with light gray shading) compared to the color of the graphical symbol for activity data point 810, which is on the higher end of color scale 815 (e.g., black).

In the example of FIG. 9, the clinician can display the histogram bin count by varying the size of a graphical symbol used to indicate each activity data point. In FIG. 9, low endurance (i.e., low frequency) events are represented by circular symbols having smaller diameter than higher endurance (i.e., high frequency) events. In FIG. 9, activity data point 905 represents a lower endurance event than activity data point 910 because the diameter of the graphical symbol for activity data point 905 is less than the diameter of the graphical symbol for activity data point 910. Additionally, when this endurance interpretation is combined with the intensity interpretation described above, the example of FIG. 9 indicates that the patient is rapidly improving because high frequency activity data point 910 is below the y=x line and is higher and further away from the origin than low frequency activity data point 905, which is also below the y=x line.

In the example of FIG. 10, the clinician can display the histogram bin count by varying the height of a graphical symbol used to indicate each activity data point. In FIG. 10, a low endurance event (i.e., low frequency) is represented by a shorter column than a high endurance (i.e., high frequency) event. In FIG. 10, activity data point 1005 represents a lower endurance event than activity data point 1010 because the height of the column for activity data point 1005 is less than the height of the column for activity data point 1010. Also, like FIG. 9, the example of FIG. 10 indicates that the patient is rapidly improving because high frequency activity data point 1010 is below the y=x line and is higher and further away from the origin than low frequency activity data point 1005, which is also below the y=x line.

Exemplary Method for Displaying Patient Activity Data from an ICD

Figure 4:
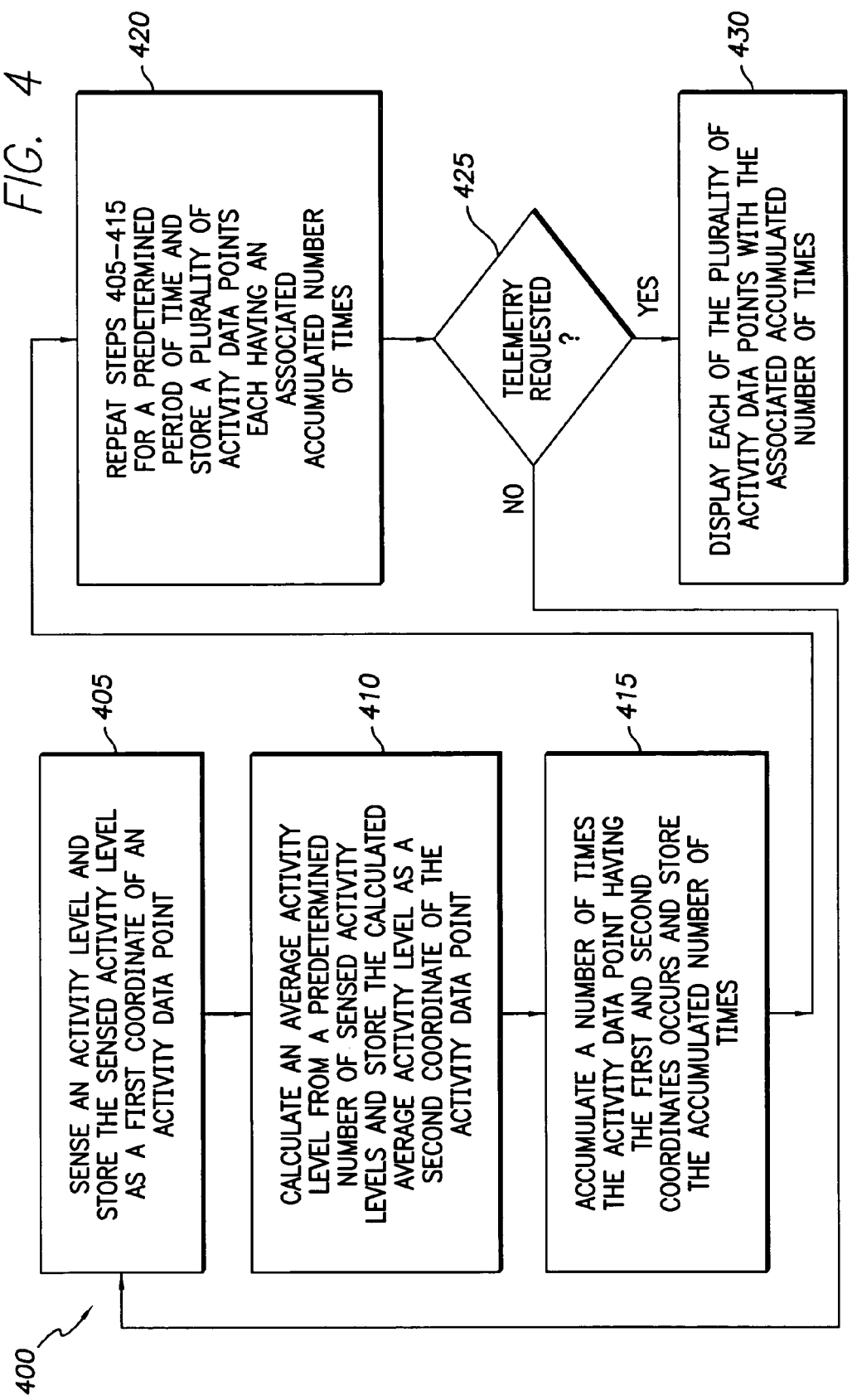
FIG. 4 is a process flowchart providing example steps for displaying patient activity data from an ICD.
Figure 5:
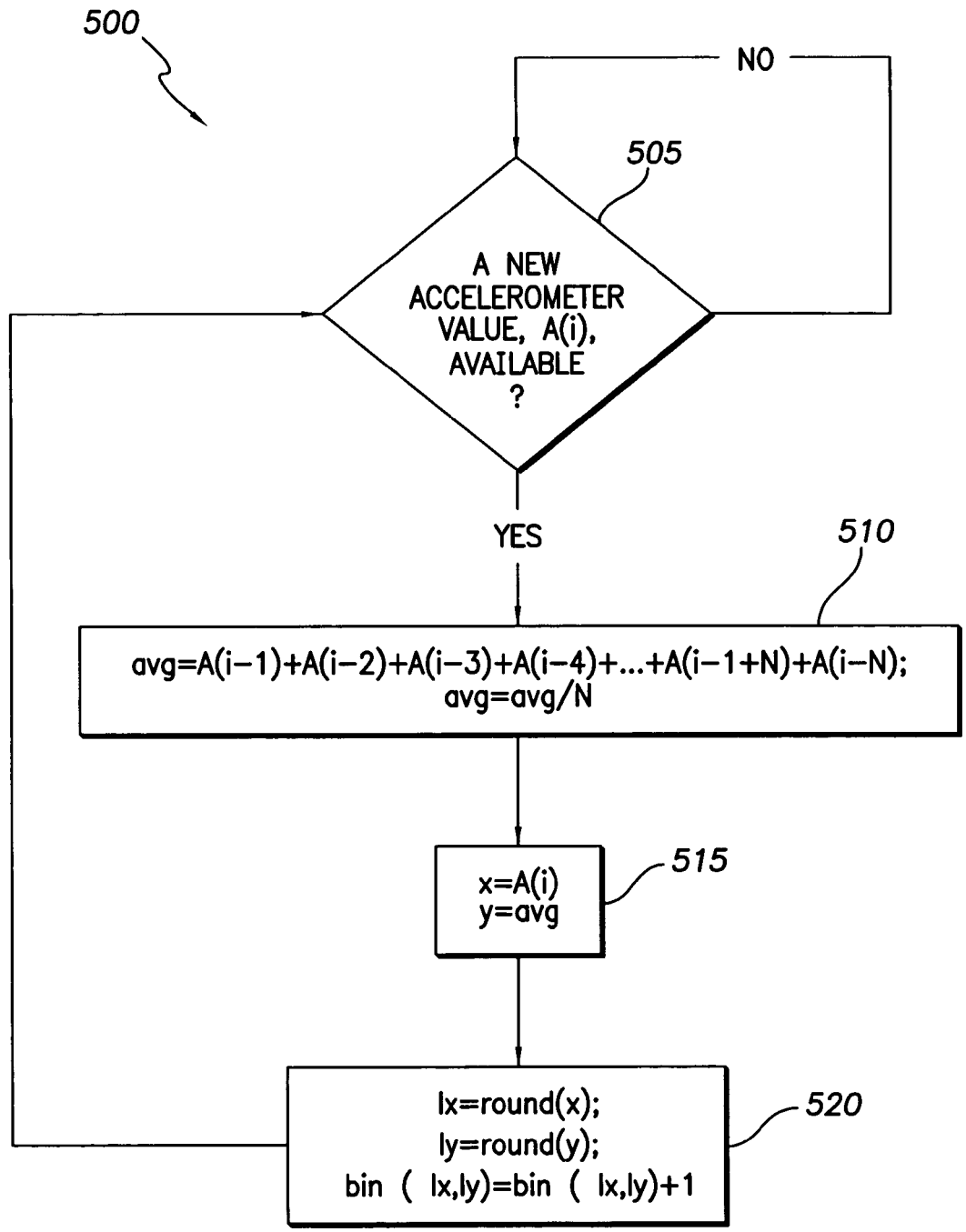
FIG. 5 is a process flowchart providing example steps in an ICD for processing accelerometer data.
Figure 6:
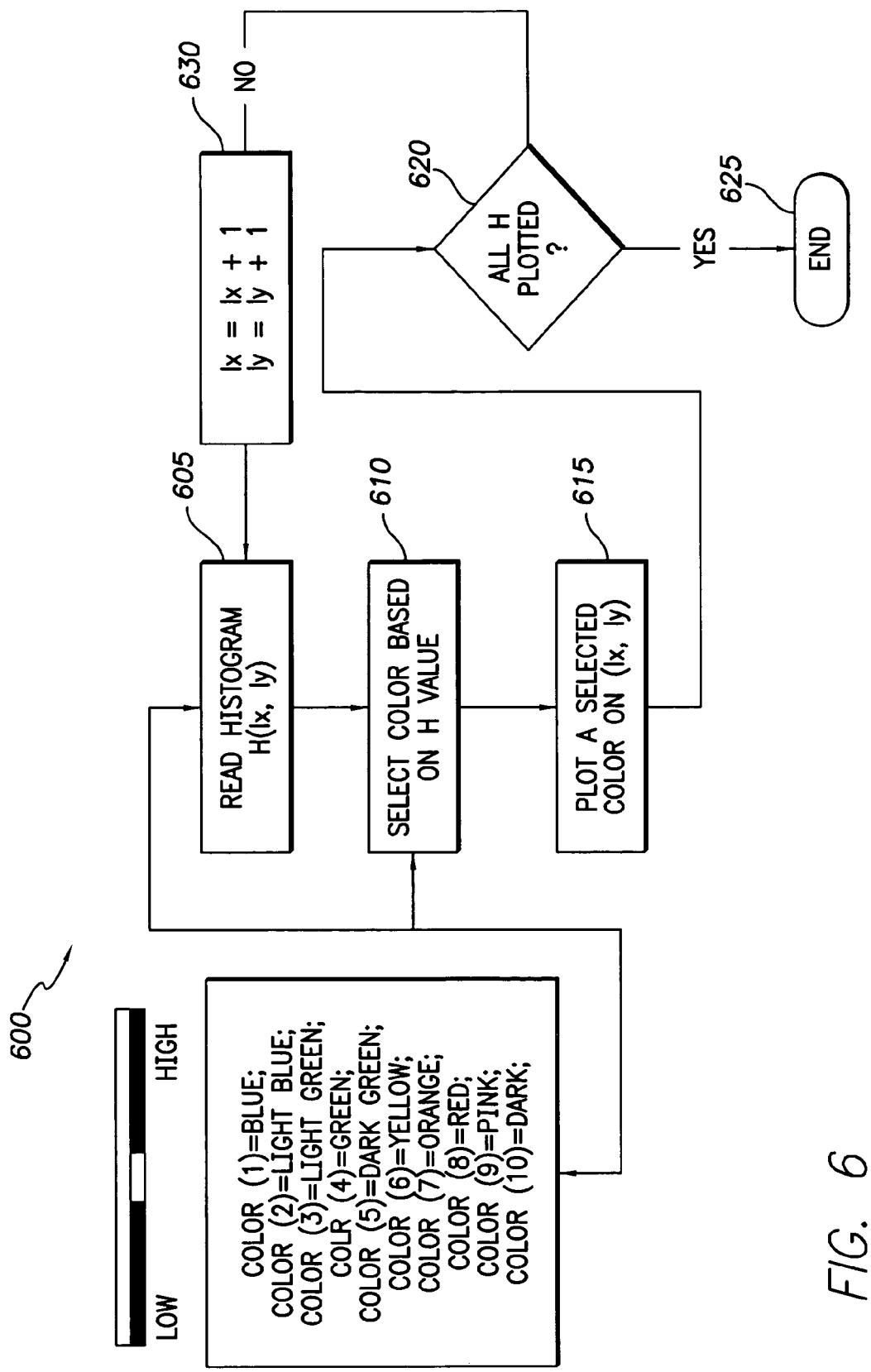
FIG. 6 is a process flowchart providing example steps in graphical user interface for displaying accelerometer data from an ICD.

In this section, example techniques are described for displaying patient activity data from an ICD. FIGS. 4-6 show process flowcharts providing example steps for displaying patient activity data from an ICD. The steps of FIGS. 4-6 do not necessarily have to occur in the order shown, as will be apparent to persons skilled in the relevant art(s) based on the teachings herein. Other operational and structural embodiments will be apparent to persons skilled in the relevant art(s) based on the following discussion. These steps are described in detail below.

FIG. 4 shows a process flowchart 400 providing steps for displaying patient activity data from an ICD. In step 405, an activity level is sensed and stored as a first coordinate of an activity data point. For example, in ICD 305 shown in FIG. 3, activity sensor 315 senses an activity level of a patient, and memory 310 stores the sensed activity level as a first coordinate of an activity data point.

In step 410, an average activity level is calculated from a predetermined number of sensed activity levels and stored as a second coordinate of the activity data point. For example, in ICD 305 shown in FIG. 3, processor 320 calculates an average activity level from a predetermined number of sensed activity levels, and memory 310 stores the calculated average activity level as a second coordinate of the activity data point.

In step 415, a number of times the activity data point having the first and second coordinates occurs is accumulated and the accumulated number of times is stored. For example, in ICD 305 shown in FIG. 3, processor 320 accumulates a number of times the activity data point having the first and second coordinates occurs, and memory 310 stores the accumulated number of times.

In step 420, steps 405-415 are repeated for a predetermined period of time and a plurality of activity data points, each having an associated accumulated number of times, is stored. For example, as described above, a sixty-day moving average window can be implemented so that only sixty day's worth of activity data is stored at a time.

In step 425, it is determined whether telemetry is requested (e.g., by a clinician). If telemetry is requested, then process 400 continues to step 430 so that the activity data can be displayed. Otherwise, if telemetry is not requested, then process 400 returns to step 405, and activity data continues to be acquired.

In step 430, each of the plurality of activity data points is displayed with the associated accumulated number of times. For example, in system 300 shown in FIG. 3, graphical user interface 325 displays the activity data points with the associated accumulated number of times. As described above with respect to FIGS. 7-9, the activity data points can be plotted in two dimensions, and the accumulated number of times associated with each activity data point (i.e., histogram bin count) can be displayed by varying the color or diameter of each activity data point. Also, as described above with respect to FIG. 10, the activity data points can be plotted in three dimensions, and the accumulated number of times associated with each activity data point (i.e., histogram bin count) can be displayed by varying the height of each activity data point. In this way, a large amount of activity data can be conveniently displayed via a single plot from which intensity of activity and endurance of activity information can be derived.

Steps 405-425 of process 400 can be implemented according to process 500, shown in FIG. 5. Steps 505-520 of process 500 can be executed by processor 320 of ICD 305, shown in FIG. 3.

In step 505, it is determined whether a new accelerometer value, A(i), is available. As described above, A(i) corresponds to a sensed activity level at a current time i.

If a new accelerometer value is available, then, in step 510, an average of N past accelerometer values (where N>0) is calculated according to equations (2) and (3) below.

$$\text{avg}=[A(i-1)+A(i-2)+\ldots+A(i-N+1)+A(i-N)] \quad (2)$$

$$\text{avg}=\text{avg}/N \quad (3)$$

In step 515, an activity data point having a first coordinate x=A(i) and a second coordinate y=avg is stored. As described above, a Poincaré plot can be generated by plotting each stored activity data point (x=A(i), y=avg).

In step 520, the first and second coordinates of the activity data point are quantized according to a round function as shown below in equations (4) and (5).

$$Ix=\text{round}(x) \quad (4)$$

$$Iy=\text{round}(y) \quad (5)$$

Each quantized Poincaré activity data point (Ix, Iy) has a corresponding rough grid histogram bin that stores an accumulated count of the same (Ix,Iy) value. This histogram bin count is updated when a match occurs. Thus, a histogram bin having the coordinates (Ix, Iy) is located, and the count for that bin is incremented by one as shown below in equation (6).

$$\text{bin}(Ix,Iy)=\text{bin}(Ix,Iy)+1$$

Step 430 of process 400 can be implemented according to process 600, shown in FIG. 6. Steps 605-630 of process 600 can be executed by graphical user interface 325, shown in FIG. 3. In this way, a clinician can download the Poincaré activity data points and associated histogram bin counts from ICD 305 to display Poincaré, intensity, and endurance information on a single plot.

In step 605, the histogram bin count for a histogram bin H(Ix, Iy) is read. In step 610, a color (1)-(10) is selected based on the value of H(Ix, Iy). For example, as described above with respect to FIG. 8, the value of the histogram bin count represents the endurance of an event, and the clinician can choose to display the histogram bin count by varying the color of a graphical symbol used to plot the corresponding activity data point. Each different color can represent a particular histogram bin count or range of histogram bin counts.

In the example of FIG. 8, activity data point 805 represents a lower endurance event than activity data point 810 because, according to color scale 815, the color of the graphical symbol for activity data point 805 is on the lower end of color scale 815 (e.g., light blue) compared to the color of the graphical symbol for activity data point 810, which is on the higher end of color scale 815 (e.g., black). As will be understood by one of skill in the art, the clinician can choose to vary graphical symbol features other than color, such as diameter (as shown in FIG. 9), height (as shown in FIG. 10), shape, and the like, to depict relative endurance of activity (i.e., exercise) events.

In step 615 the selected color is used to plot the Poincaré activity data point (Ix, Iy). In step 620, it is determined whether the bin counts for all of the histogram bins H have been plotted. If the bin counts for all of the histogram bins H have not been plotted, then, in step 630, the value of Ix is incremented by one and the value of Iy is incremented by one, and, in step 605, the bin count for a histogram bin H(Ix+1, Iy+1) is read. If the bin counts for all of the histogram bins H have been plotted, then, in step 625, process 600 ends.

CONCLUSION

Example methods and systems for displaying patient activity data from an ICD have been described herein. As noted elsewhere, these example embodiments have been described for illustrative purposes only, and are not limiting. Other embodiments are possible and are covered by the methods and systems described herein. Such embodiments will be apparent to persons skilled in the relevant art(s) based on the teachings contained herein. Thus, the breadth and scope of the methods and systems described herein should not be limited by any of the above-described exemplary embodiments, but should be defined only in accordance with the following claims and their equivalents.

What is claimed is:

1. A system for displaying patient activity data, comprising:
    an implantable cardiac device (ICD), the ICD comprising:
        at least one sensor that senses an activity level related to movement of a patient;
        a memory that stores the activity level as a first coordinate of an activity data point;
        a processor that generates an average activity level from a predetermined number of sensed activity levels, that stores the average activity level in the memory as a second coordinate of the activity data point, that accumulates a number of times the activity data point having the first and second coordinates occurring occurs, and that stores in the memory the accumulated number of times; and
    a graphical user interface that retrieves from the memory of the ICD a plurality of activity data points, each having an associated accumulated number of times, and displays each of the plurality of activity data points with the associated accumulated number of times.

2. The system of claim 1, wherein the processor quantizes the first coordinate and the second coordinate and accumulates a number of times an activity data point having the quantized first and second coordinates occurs.

3. The system of claim 1, wherein the graphical user interface displays the associated accumulated number of times using a plurality of colors.

4. The system of claim 1, wherein the graphical user interface displays the associated accumulated number of times using a plurality of sizes of a graphical symbol.

5. The system of claim 4, wherein the graphical user interface displays the associated accumulated number of times using a plurality of diameters of the graphical symbol.

6. The system of claim 4, wherein the graphical user interface displays the associated accumulated number of times using a plurality of heights of the graphical symbol.

7. The system of claim 1, wherein the graphical user interface displays an intensity of each of the plurality of activity data points.

8. The system of claim 1, wherein the graphical user interface displays an endurance of each of the plurality of activity data points.

9. A system for displaying patient activity data, comprising:
    an implantable cardiac device (ICD) the ICD comprising:
        sensor means for sensing an activity level related to movement of a patient;
        storage means for storing the activity level as a first coordinate of an activity data point;
        processing means for generating an average activity level from a predetermined number of sensed activity levels, wherein the storage means stores the average activity level as a second coordinate of the activity data point;
        wherein the processing means further accumulates a number of times the activity data point having the first and second coordinate occurs, and wherein the storage means further stores the accumulated number of times; and
    display means for retrieving from the storage means a plurality of activity data points, each having an associated accumulated number of times, and displaying each of the plurality of activity data points with the associated accumulated number of times.

10. The system of claim 9, wherein the display means displays an intensity of each of the plurality of activity data points.

11. The system of claim 9, wherein the display means displays an endurance of each of the plurality of activity data points.

* * * * *